(12) United States Patent
Alfery et al.

(10) Patent No.: US 7,040,312 B2
(45) Date of Patent: May 9, 2006

(54) PERILARYNGEAL ORAL AIRWAY WITH FLEXIBLE TIP GUIDE

(75) Inventors: David D. Alfery, Nashville, TN (US); Brad Quinn, Indianapolis, IN (US)

(73) Assignee: Engineered Medical Systems, Inc., Indianapolis, IN (US)

( * ) Notice: Subject to any disclaimer, the term of this patent is extended or adjusted under 35 U.S.C. 154(b) by 33 days.

(21) Appl. No.: 10/150,549

(22) Filed: May 16, 2002

(65) Prior Publication Data

US 2003/0213492 A1  Nov. 20, 2003

(51) Int. Cl.
*A61M 16/00* (2006.01)

(52) U.S. Cl. .................... 128/200.26; 128/207.14; 128/207.15

(58) Field of Classification Search .......... 128/207.14, 128/200.26, 207.15
See application file for complete search history.

(56) References Cited

U.S. PATENT DOCUMENTS

| | | |
|---|---|---|
| 3,756,244 A | 9/1973 | Kinnear et al. |
| 3,774,616 A | 11/1973 | White |
| 3,908,665 A | 9/1975 | Moses |
| 4,046,139 A | 9/1977 | Horn |
| 4,054,135 A | 10/1977 | Berman |
| 4,063,561 A | 12/1977 | McKenna |
| 4,067,331 A | 1/1978 | Berman |
| 4,263,921 A | 4/1981 | Trugillo |
| D261,442 S | 10/1981 | Anderson |
| 4,338,930 A | 7/1982 | Williams |
| 4,383,534 A | 5/1983 | Peters |
| 4,454,887 A | 6/1984 | Kruger |
| 4,497,324 A | 2/1985 | Sullivan et al. |
| 4,502,482 A | 3/1985 | DeLuccia |
| 4,509,514 A | 4/1985 | Brain |
| 4,527,553 A | 7/1985 | Upsher |
| 4,612,927 A * | 9/1986 | Kruger .................. 128/200.26 |
| 4,683,879 A | 8/1987 | Williams |
| 4,796,640 A | 1/1989 | Webler |
| 4,825,858 A | 5/1989 | Frankel |
| 4,827,910 A | 5/1989 | Mathews, III |
| 4,832,020 A | 5/1989 | Augustine |
| 4,848,331 A | 7/1989 | Northway-Meyer |
| 4,852,565 A | 8/1989 | Eisele |
| 4,919,126 A | 4/1990 | Baildon |
| 4,976,261 A | 12/1990 | Gluck et al. |
| 5,038,766 A | 8/1991 | Parker |
| 5,057,106 A | 10/1991 | Kasevich et al. |
| 5,163,423 A | 11/1992 | Suzuki |
| 5,174,283 A | 12/1992 | Parker |
| 5,203,320 A | 4/1993 | Augustine |

(Continued)

FOREIGN PATENT DOCUMENTS

GB  1535060  12/1978

(Continued)

*Primary Examiner*—Mital Patel
(74) *Attorney, Agent, or Firm*—Swanson & Bratschun LLC

(57) ABSTRACT

An oral airway consists of an elongate tubular member having a leading distal end and a proximal end, the leading distal end leading the elongate tubular member as it is inserted into the mouth and pharynx of a patient. An opening at the leading distal end of the elongate tubular member is inclined so that a posterior portion of the distal portion extends beyond an anterior portion of the distal end. A flexible tip portion extends distally beyond the opening to aid in insertion of the oral airway into the mouth and pharynx of a patient. The tip is configured to flex toward the opening as it abuts tissue within the mouth and pharynx of a patient.

11 Claims, 6 Drawing Sheets

U.S. PATENT DOCUMENTS

| | | |
|---|---|---|
| 5,295,489 A | 3/1994 | Bell et al. |
| 5,303,697 A | 4/1994 | Brain |
| 5,309,906 A * | 5/1994 | LaBombard ............ 128/207.14 |
| 5,323,771 A | 6/1994 | Fisher et al. |
| 5,339,805 A | 8/1994 | Parker |
| 5,357,954 A | 10/1994 | Shigezawa et al. |
| 5,365,940 A | 11/1994 | Teves |
| 5,443,063 A | 8/1995 | Greenberg |
| 5,477,851 A | 12/1995 | Callaghan et al. |
| 5,562,608 A | 10/1996 | Sekins et al. |
| 5,622,182 A | 4/1997 | Jaffe |
| 5,653,229 A | 8/1997 | Greenberg |
| 5,720,275 A | 2/1998 | Patil |
| 5,743,254 A | 4/1998 | Parker |
| 5,743,258 A | 4/1998 | Sato et al. |
| 5,746,202 A | 5/1998 | Pagan |
| 5,771,889 A | 6/1998 | Pagan |
| 5,819,733 A | 10/1998 | Bertram |
| 5,853,004 A | 12/1998 | Goodman |
| 5,873,362 A | 2/1999 | Parker |
| 5,878,745 A | 3/1999 | Brain |
| 5,896,858 A | 4/1999 | Brain |
| 5,937,859 A | 8/1999 | Augustine et al. |
| 5,937,860 A | 8/1999 | Cook |
| 5,979,445 A | 11/1999 | Neame et al. |
| 5,983,897 A | 11/1999 | Pagan |
| 6,003,514 A | 12/1999 | Pagan |
| 6,012,452 A | 1/2000 | Pagan |
| 6,021,779 A | 2/2000 | Pagan |
| 6,053,166 A | 4/2000 | Gomez .................. 128/200.26 |
| 6,070,581 A | 6/2000 | Augustine et al. |
| 6,079,409 A | 6/2000 | Brain |
| 6,095,144 A | 8/2000 | Pagan |
| 6,116,243 A | 9/2000 | Pagan |
| 6,119,695 A | 9/2000 | Augustine et al. ..... 128/207.15 |
| 6,152,136 A | 11/2000 | Pagan |
| 6,240,922 B1 | 6/2001 | Pagan |
| 6,311,688 B1 | 11/2001 | Augustine et al. |
| 6,318,367 B1 | 11/2001 | Mongeon |
| 6,321,749 B1 | 11/2001 | Toti et al. ............... 128/207.14 |
| 6,338,343 B1 | 1/2002 | Augustine et al. |
| 6,386,199 B1 | 5/2002 | Alfery |
| 6,526,977 B1 * | 3/2003 | Gobel .................... 128/207.14 |
| 2001/0041861 A1 | 11/2001 | Gobel |

FOREIGN PATENT DOCUMENTS

| | | |
|---|---|---|
| WO | WO 92/13587 | 8/1992 |
| WO | WO 99/45991 | 9/1999 |

* cited by examiner

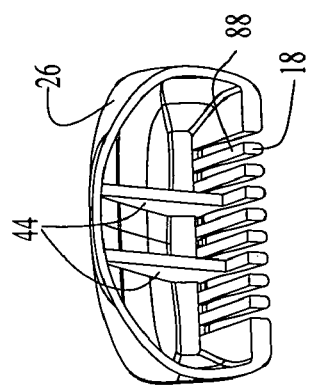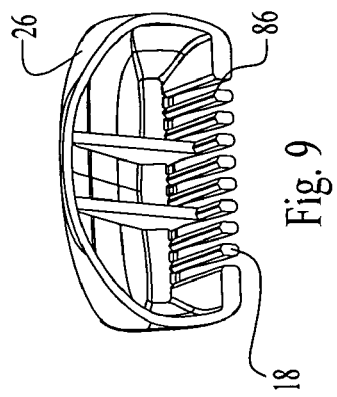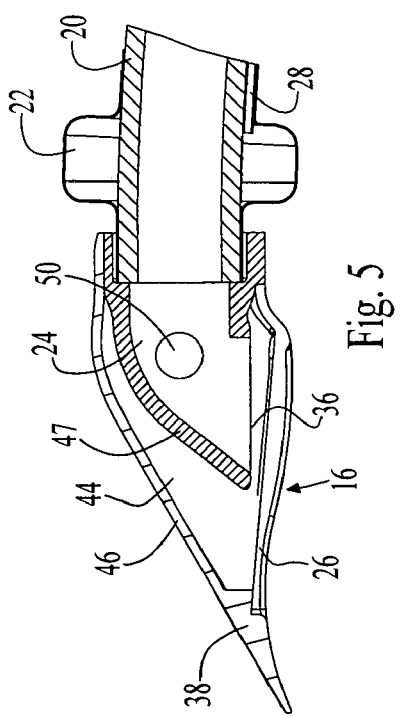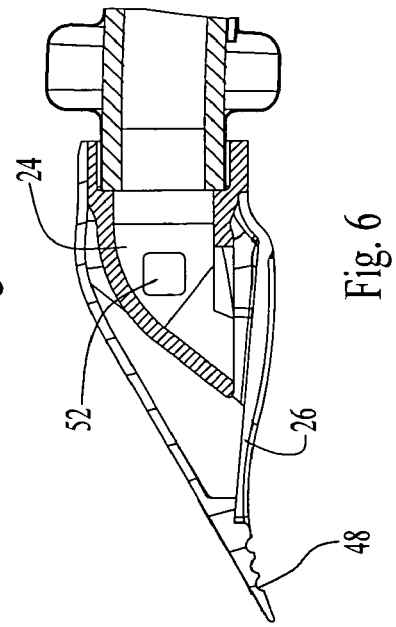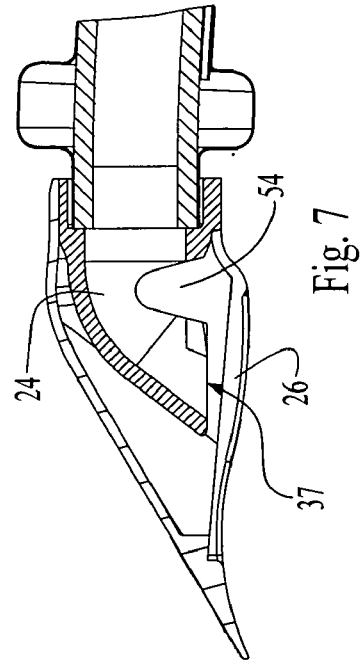

PERILARYNGEAL ORAL AIRWAY WITH FLEXIBLE TIP GUIDE

TECHNICAL FIELD

The present invention relates generally to a class of medical devices commonly referred to as oral airways and supraglottic airways which are inserted through a patient's mouth and into the patient's pharynx while the patient is undergoing general anesthesia or is undergoing respiratory treatment such as is carried out with cardiopulmonary resuscitation. More specifically, the present invention is directed to a perilaryngeal oral airway and perilaryngeal supraglottic airway which is capable of acting as an endotracheal tube guide and which seats deep in a patient's hypopharynx to prevent the soft tissue of the glottis and epiglottis from obstructing the airway.

BACKGROUND ART

Oral airways were introduced into the practice of anesthesia and cardiopulmonary resuscitation several decades ago for two basic purposes. First, they prevent the patient's biting down on and occlusion of a previously placed oral endotracheal tube. Second, and most important, oral airways help to provide a patent airway that allows positive pressure ventilation to be carried out by the practitioner. More recently, some oral airways have been developed to facilitate blind (not visually directed) placement of an endotracheal tube.

For most patients, mask ventilation is carried out successfully by insertion of an oral airway and by a variety of physical adjustments, such as extension of the patient's head and elevation of the patient's jaw. However, in some patients, no matter what physical adjustments are made or the particular oral airway which is inserted, mask ventilation cannot be successfully achieved. Such cases are literally life-threatening as hypoxemia and death can quickly ensue if the patient's blood is deprived of oxygen due to a lack of ventilation.

When mask ventilation (even with the use of an oral airway) cannot be carried out, there are multiple mechanisms responsible. Most significantly, soft tissue structures in the hypopharynx (the area between where conventional oral airways end and the glottis opens into the trachea) collapse inwardly and obstruct airflow. This collapse occurs from both an antero-posterior direction, as well as from the sides of the hypopharynx. Unfortunately, all oral airways which have been introduced into practice to date end bluntly well above the epiglottis (the cartilaginous structure just above the glottis or laryngeal opening) and glottis and thus place patients at risk for significant airway obstruction. Another mechanism of airway obstruction which occurs while using oral airways is the patient having large lips covering the outside opening of the oral airway with subsequent inadequate airflow through the nasal passages (due to the solid posterior wall of the airway limiting passage of air into the airway at the level of the nasopharynx).

Additionally, most known oral airways are comprised of a hard plastic material throughout their length with no variation in softness between one end of the oral airway and the opposite end. As a result, the distal end (i.e., the end which first enters the mouth and passes down into the pharynx of the patient) often bruises or otherwise damages soft mucosal surfaces of the patient during insertion or once the oral airway has been seated in place.

Representative prior art airways include Baildon, U.S. Pat. No. 4,919,126, which discloses an oral airway formed of plastic which includes an air passageway extending longitudinally through the airway. The distal end has a projecting solid anterior portion which serves as an "epiglottis elevator." As such, the oral airway is blunt-shaped in configuration and ends well above the glottis. For this reason, the Baildon oral airway suffers from the problems discussed above in that it fails to provide any structure to prevent the collapse of soft tissue structures in the hypopharynx.

Berman, U.S. Pat. Nos. 4,054,135 and 4,067,331, relate to an intubating pharyngeal airway having a side access for passage of an endotracheal tube. The airway includes a blunt end on the anteriorly extending wall which is designed to fit into the vallecula (area between the epiglottis and tongue). Accordingly, the devices disclosed in both of Berman's patents are similar to the device of Baildon in that they can detrimentally allow soft tissue structures to invaginate inward and thereby occlude the passage of air.

Moses, U.S. Pat. No. 3,908,665, discloses an oro-pharyngeal airway wherein the outer diameter of the body portion progressively increases from the end closest to the mouth to the opposite end thereof so as to relieve any obstruction to the flow of air by the base of the tongue falling back on the posterior pharyngeal wall. However, the airway of Moses likewise suffers from the problems discussed in detail above in that the blunt-shaped end terminates well above the glottis, thereby allowing possible soft tissue obstruction to occur.

Augustine, U.S. Pat. No. 5,203,320, discloses a tracheal intubation guide which similarly seats above the glottis. Moreover, the device of Augustine functions as a guide for placing an endotracheal tube in a "blind" manner and is neither designed for nor could it possibly function to allow mask ventilation to be carried out.

In addition, for some patients it is important to use an airway device which provides a seal within the patient's airway (trachea, oro- or hypopharynx) in order to better allow positive pressure ventilation to be accomplished. These airways are referred to herein as supraglottic airways. Traditionally, this has been achieved by using an endotracheal tube passed between a patient's vocal cords. In an effort to avoid the deleterious effects of tracheal intubation (e.g., bronchospasm, dental injury and cardiovascular stimulation), the laryngeal mask airway ("LMA") has been introduced into clinical practice. The LMA is illustrated and described in Brain, U.S. Pat. No. 4,509 5149. While providing a seal with which to administer positive pressure ventilation, there are several potential problems when using an LMA. First, the device is easily malpositioned so that ventilation is not possible, for example, by virtue of the epiglottis bending back over the glottis and thereby obstructing air flow. Second, by directly covering the glottic aperture, trauma to the glottic structures (arytenoid cartilages, vocal cords) can occur. In addition, the cost of this product (over $200) becomes a factor when limitations to reuse occur due to physical damage of the device or accidental loss. Third, as a reusable product, the hazard of cross-contamination from one patient to another cannot be completely eliminated.

Because of the above-limitations of the LMA, a cuffed oro-pharyngeal airway has been introduced into clinical practice. Greenberg, U.S. Pat. No. 5,443,063, describes such a device as an oro-pharyngeal cuff placed over a conventional oral airway. However, this device has several significant limitations which prevent it from functioning adequately. First, the airway suffers from the problems of those previously discussed in that it ends well above the glottis, thereby allowing soft tissue obstruction to impair the flow of oxygen to the lungs. Second, with the cuff placed so far proximally in the oro-pharynx, the device tends to push itself out of the patient's mouth, thereby requiring that the device be secured in place by means of a strap placed around the patient's head. Finally, the cuff is positioned so far proximally in the patient's airway that it often allows leakage of oxygen and anesthetic gases around the cuff, thereby preventing the formation of an air-tight seal. This, of course, makes positive pressure ventilation impossible in those patients.

Several oral airways, including those described in the patents to Berman and Augustine, have been introduced into clinical practice in an effort to provide a means to accomplish blind intubation of a patient's trachea with an endotracheal tube (or to facilitate fiberoptic intubation). These devices end well above the glottic opening and thus function poorly in terms of reliably directing the end of an endotracheal tube into the glottis with blind passage. As a result, the hard distal end of the endotracheal tube may be directed against the structures which surround the glottic opening (arytenoid, cuneiform and corniculate cartilages, epiglottis, aryepiglottic folds) and cause damage to these structures or their soft tissue surfaces. Further, that damage may result in hemorrhage which obscures vision if subsequent placement of the endotracheal tube by means of a fiberoptic device is attempted. Other prior art has attempted to better direct an endotracheal tube into the glottis by having walls which surround and thus engage the arytenoid cartilages or which have projections which physically enter in between those cartilages. Representative are Patil, U.S. Pat. No. 5,720,275; Krüger, U.S. Pat. No. 4,612,927; and Williams, U.S. Pat. No. 4,338,930. However, these structures have hard advancing surfaces which can likewise cause trauma.

Recently, a version of the LMA which is meant to facilitate blind intubation with an endotracheal tube has been introduced into clinical use which attempts to surmount the problems of a misguided endotracheal tube causing trauma to perilaryngeal and glottic structures. This LMA is described in Brain, U.S. Pat. No. 5,896,858. However, in addition to sharing the above discussed problems common to all LMA's, this device relies on precise positioning so that a movable flap raises an obstructing epiglottis out of the way of an advancing endotracheal tube. Because the attached flap resides within the body of the LMA it does not physically contact the epiglottis upon insertion, but rather the advancing endotracheal tube pushes the flap up against the epiglottis to move it out of the way and thus open the glottic aperture for the endotracheal tube to enter. Perfect alignment of the recessed flap with the epiglottis is thus necessary to reliably accomplish blind placement of the endotracheal tube. However, LMA's occupy a somewhat variable and inconsistent position within the hypopharynx in relation to the precise anatomic location of the glottis (due to anatomic variability among patients as well as the distensible nature of the proximal epiglottis and hypopharynx where it resides). As a result, blind intubation with an endotracheal tube with this device can also result in tissue trauma by virtue of its advancing end being misdirected.

Supraglottic airways are sometimes used in anesthetized patients undergoing surgery within the oral cavity or on the head and neck. As such, the presence of the breathing tube can be a physical impediment to the operating surgeon. Known oral airways are too rigid to allow the airway to be moved from the surgical field. Further, a version of the LMA which is made using a flexible reinforced breathing channel suffers from the limitations common to LMAs discussed above.

Another problem with known airway devices, including LMA's, is the difficultly that can be encountered in inserting the device into the mouth and pharynx of a patient. This problem can be easily understood by reference to FIG. 12 where it is seen that the transition between the oral cavity and the hypopharynx requires turning approximately 90° or more. Executing this turn with known devices can be difficult and can cause damage to the soft mucosal tissue that makes up the posterior surface of the pharynx as it is engaged by the airway device.

Pagan, U.S. Pat. No. 5,983,897, is directed to an LMA structure including a leading tip 21 which projects forwardly beyond the upper and lower cuff members of the LMA to provide a stiffer leading edge than that provided by the cuffs to help guide the mask portion into the correct location in a patient. This leading tip has several serious shortcomings. First, it is intended to be a stiff structure which increases the risk of harm to soft tissue it contacts. Furthermore, the tip is not intended to bend to follow the contours of the oral cavity, pharynx and hypopharynx as it is placed within a patient. Therefore, because it projects outwardly from the LMA structure, it effectively lengthens the LMA structure, further enhancing the difficulty in inserting the airway within a patient without harming soft tissue. Finally, while FIG. 2 of the Pagan patent shows a preformed bend in the leading tip, this bend is actually opposite the direction of the larynx as the device is inserted into the pharynx of a patient and thus does not effective guide the LMA while minimizing patient trauma.

The present invention is intended to overcome one or more of the problems discussed above.

SUMMARY OF THE INVENTION

A first aspect of the present invention is an elongate tubular member having a leading distal end and a proximal end, with the leading distal end leading the elongate tubular member as it is inserted into the mouth and pharynx of a patient. An opening is provided at the leading distal end that is inclined so that a posterior portion of the distal end extends beyond an anterior portion of the distal end. A flexible tip portion extends distally beyond the opening to aid insertion of the oral airway into the mouth and pharynx of a patient. The tip is configured to flex toward the opening as the tip abuts tissue within the mouth and pharynx of a patient. The tip is preferably sufficiently flexible to flex without harming the tissue it encounters. In one embodiment the flexibility is aided by the tip being made of a material having a durometer of about 70 or less. The flexibility may further be aided by the flexible tip tapering toward its distal end. The flexibility may further be aided by the flexible tip having lateral grooves. In one embodiment the oral airway further includes a housing at the distal end of the elongate tubular member which surrounds the opening. The flexible tip portion is attached to the housing. In this embodiment the housing is preferably configured to flex toward the opening about the distal end of the elongate tubular member as the tip abuts tissue as it is inserted into the mouth and pharynx of a patient. The elongate tubular member may include an elbow attached to the distal end which defines the opening. In this embodiment the housing further comprises a pair of spaced ribs extending between an inner surface of a posterior wall and the posterior portion of the distal end of the elongate tubular member, with this posterior portion being part of the elbow. The spaced ribs deflect to receive the posterior portion of the elbow as the elongate tubular member of the housing is flexed toward the opening. The housing may further include an opening corresponding to the tubular member opening. In this embodiment the housing may further include flexible bars extending axially of the tubular member covering the housing opening. The flexible bars deflect laterally as the housing member is flexed toward the opening.

Another aspect of the invention is a method of providing an oral airway to a patient. The method includes providing an elongate tubular member having a leading distal end and a proximal end with the leading distal end leading as the elongate tubular member is inserted into the mouth and pharynx of a patient. An opening is provided at the leading distal end that is inclined so that a posterior portion of the distal end extends beyond an anterior portion of the distal end. A flexible tip portion is provided that extends distally beyond the opening. The leading distal end of the elongate tubular member is inserted into the mouth of a patient and axially advanced into the mouth and pharynx of the patient. The flexible tip is flexed in the direction of a patient's larynx as the flexible tip abuts tissue within the mouth and pharynx of the patient to guide the oral airway in to the patient's hypopharynx. The leading distal end of the elongate tubular member is seated within the hypopharynx with the opening adjacent to the glottis of the patient and the flexible tip on the esophagus side of the arytenoid cartilage.

Yet another aspect of the present invention is an oral airway consisting of an elongate tubular member having a leading distal end and a proximal end, with the leading distal end leading the elongate tubular member as it is inserted in to the mouth and pharynx of a patient. An opening is provided proximate the distal end for delivering air to a patient. The elongate tubular member is configured to place the opening near the glottis of a patient with the distal end seated in the hypopharynx of the patient. A cuff is provided on the elongate tubular member near the opening. The cuff has an inflated and deflated state and is sized so that with the distal end seated in the hypopharynx of a patient and the cuff in its inflated state, the cuff forms a seal with the tissue of the pharynx or hypopharynx surrounding the cuff regardless of the anatomy of the patient. The cuff is formed of a thin-walled foil having a wall thickness which prevents formation of fold loops of a diameter sufficient to allow the passage of air which effectively breaches the seal. The wall thickness is less than about 0.03 mm and is preferably between about 0.03–0.005 mm.

The present invention provides an oral airway for reliably holding soft tissue structures away from the laryngeal opening to assure adequate airflow to a patient. The invention also provides a supraglottic airway which holds soft tissues in the vicinity of the laryngeal opening apart and which provides for seating of the distal end of the oral airway in a consistent and precise manner adjacent the larynx or glottis aperture for facilitating positive pressure ventilation by anesthesia circuit, resuscitation mask or ventilator. The present invention further provides a flexible leading tip that is configured to bend toward the larynx as the airway is inserted into the mouth and pharynx of a patient. This allows the tip to function as a guide facilitating proper placement of the device within a patient. Moreover, because the tip is flexible and the housing itself is flexible in that they can bend in the direction of the larynx, the bending effectively shortens the length of the housing as it makes the critical bend into the pharynx, thereby minimizing trauma to the contacted tissue. The flexible tip is further configured to lodge on the esophagus side of the arytenoid cartilage which helps position the opening of the airway proximate the laryngeal opening. These many advantages are provided by a structure which is rigid enough to assure proper placement and to prevent inadvertent kinking of the airway, yet soft enough to minimize the risk of injury to the sensitive tissue of the oral cavity, pharynx and hypopharynx. The flexible breathing tube can be manipulated by an operating surgeon to displace it from the operating field within an oral cavity or pharynx. The ultra-thin walled cuff of the present invention allows providing a single-sized cuff that can effectively form a seal in the pharynx or hypopharynx of a patient, regardless of the patient's size or anatomy. Finally, all these many advantages are provided by an airway which is relatively easily manufactured from inexpensive materials, thereby promoting its widespread use and making its many advantages readily available.

BRIEF DESCRIPTION OF THE DRAWINGS

FIG. 5 is a cross-sectional view of the perilaryngeal oral airway of FIG. 1 taken along line 5—5 of FIG. 4;

FIG. 6 is an alternate embodiment of the portion of the perilaryngeal oral airway depicted in FIG. 5;

FIG. 7 is an alternate embodiment of the portion of the perilaryngeal oral airway depicted in FIG. 5;

FIG. 8 is a cross-sectional view of the housing of the perilaryngeal oral airway of FIG. 1 taken along line 8—8 of FIG. 1 and rotated to illustrate a cross-section of the flexible bars;

FIG. 9 is an alternate embodiment of the housing depicted in FIG. 8;

DETAILED DESCRIPTION OF THE PREFERRED EMBODIMENT

The perilaryngeal oral airway described herein is a preferred embodiment of a perilaryngeal oral airway structure including a flexible tip for guiding insertion of the perilaryngeal oral airway into the mouth and pharynx of a patient. Further alternative structures of perilaryngeal oral airways are disclosed in Applicant's co-pending application Ser. No. 09/409,295, now U.S. Pat. No. 6,386,199, the contents of which are incorporated herein in their entirety by reference. It should be appreciated by those skilled in the art that the perilaryngeal oral airway structures disclosed in U.S. Pat. No. 6,386,199, could be modified to include the flexible tip feature described herein.

Figure 1:
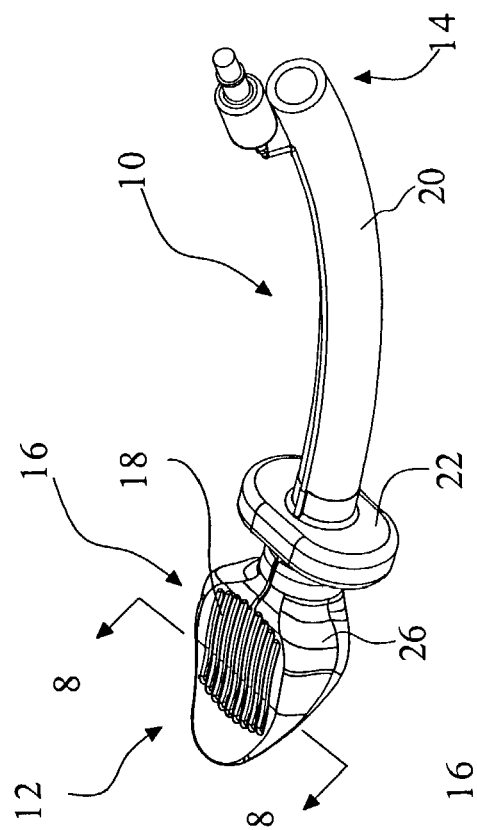
FIG. 1 is a perspective view of a perilaryngeal oral airway in accordance with one embodiment of the present invention.
Figure 2:
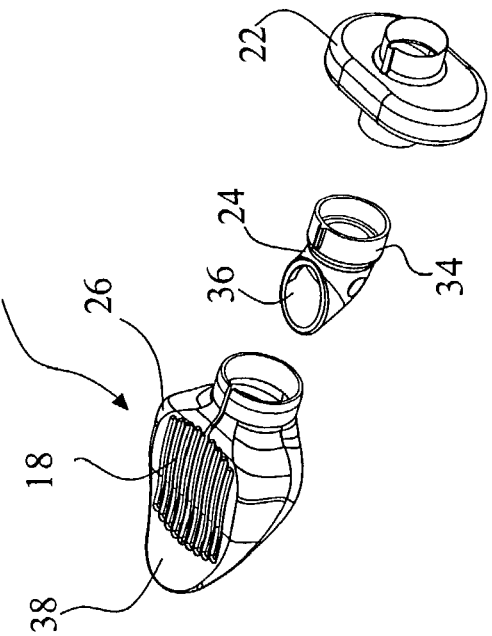
FIG. 2 is an exploded view of the perilaryngeal oral airway of FIG. 1.

A perilaryngeal oral airway ("PLA") 10 is shown in an assembled perspective view in FIG. 1. The PLA can generally be described as an elongate tubular member having a distal end 12 and a proximal end 14. An opening 16 is provided on an anterior portion of the distal end and a number of flexible bars 18 extend axially across the opening 16.

The PLA of FIG. 1 includes at least the following components: a breathing tube 20, an inflatable cuff 22, an elbow 24, a housing 26 and a pilot tube 28 having a self-sealing valve 30 on its proximal end. When assembled as illustrated in FIG. 1, the inflatable cuff 22 receives the breathing tube 20 and is located near the distal end 32 of the breathing tube 20. The elbow 24 includes a collar 34 which receives the distal end of the breathing tube 20. The breathing tube 20 has an anterior radius or bend and the elbow has an opening 36 which opens toward the anterior radius. The opening 36 is inclined so that a posterior portion of a distal end of the elbow extends beyond an anterior portion of the distal end of the elbow. The flexible housing 26 receives the elbow and the opening 36 is located adjacent the opening 16 in the housing 26. A plurality of axial flexible bars 18 are integrally formed with the housing 26 and lie over the opening 16. The housing further includes a flexible tip 38 which extends distally beyond the housing opening 16 which will be described in greater detail below. A distal end of the pilot tube is in fluid communication with the inflatable cuff to allow for selective inflation or deflation of the cuff. The breathing tube 20, flexible collar 22, elbow 24, housing 26 and pilot tube 28 may be held together by sonic, heat or adhesive bonding as dictated by the particular materials selected for each component.

The breathing tube 20 is preferably formed of a material such as polyvinylchloride or other thermoplastic that is relatively axially rigid yet radially flexible so that when inserted into the mouth, oral cavity and pharynx of a patient, it may follow the anatomical contours. It is also preferably sufficiently flexible so that a surgeon operating on the oral cavity or pharynx with the PLA in place can axially deflect the tubular member out of the operating theater. The tubular member further is radially robust to not kink during insertion or manipulation. Although not shown, the tubular member may include wire reinforcing wound into its wall.

The elbow 24 is made of a relatively stiff and inflexible thermoplastic, such as polyvinylchloride, to help it guide the insertion of an endotracheal tube or other instrument for insertion into the trachea of a patient in a manner which will be discussed below. Rigidity of the elbow 24 also provides some measure of structural support for the housing 26.

Figure 3:
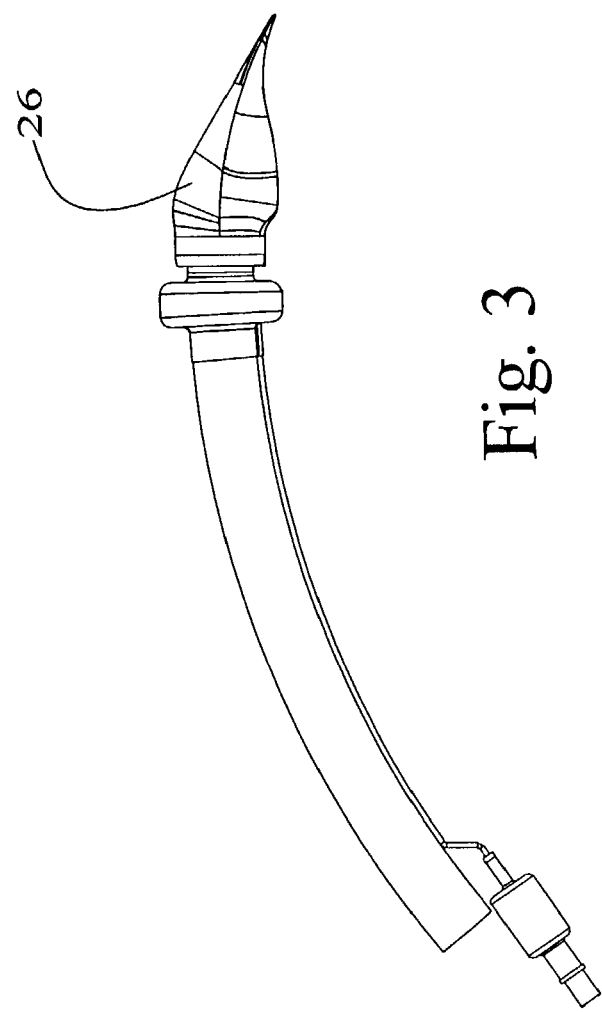
FIG. 3 is a side elevational view of the perilaryngeal oral airway of FIG. 1.
Figure 4:
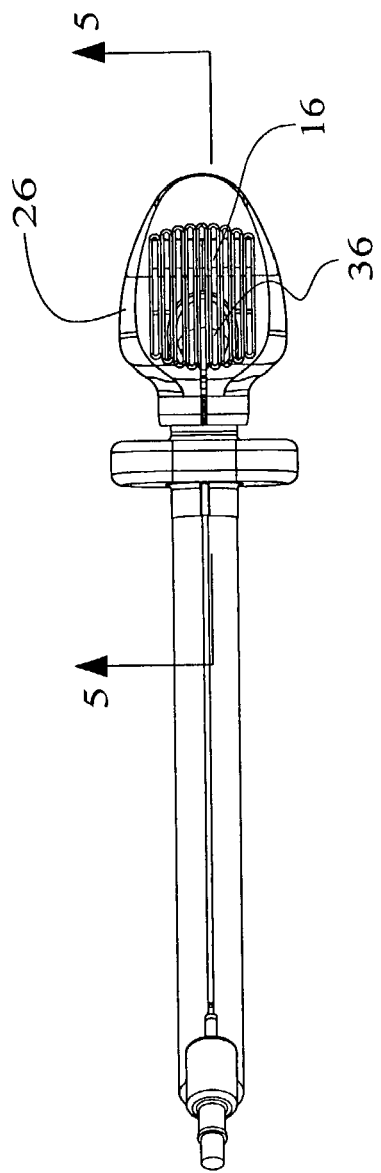
FIG. 4 is a bottom or anterior plan view of the perilaryngeal oral airway of FIG. 1.

The housing 26 is a generally wedge-shaped configuration which is perhaps best viewed in FIGS. 3 and 4. The housing is made of a material that is relatively flexible and soft so that there is some give as the housing is inserted into the patient. The particular firmness of the housing must strike a balance between the need to hold hypopharyngeal and perilaryngeal structures away from the opening, the need to move soft tonsillar and oral-pharyngeal tissue to the side as the oral airway is inserted and the desire for the oral airway to be able to bend inwardly when inserted through the back of a patient's mouth. In addition, the tip 38 must be sufficiently soft and pliable to bend during insertion both to guide the oral airway into the patient's hypopharynx and to effectively shorten the length of the housing as it must turn what may be in excess of 90° between the patient's oral cavity and the patient's hypopharynx. To help achieve this balance, the housing is preferably made of a non-toxic polyvinylchloride having a durometer of about 80 Shore A or less. In one embodiment an approximately 70 Shore A durometer (specifically, 68) was successfully used. Referring to FIG. 8, the housing includes a pair of internal support ribs 44 that are laterally spaced relative to one another. As seen in FIG. 5, when assembled the support ribs 44 extend between a posterior wall 46 of the housing and a posterior portion 47 of the elbow 24.

The flexible tip 38 of the housing 26 may take several forms. In one embodiment, the tip 38 tapers toward the distal end as illustrated in FIG. 5. In another embodiment illustrated in FIG. 6, the distal end may have a plurality of lateral grooves 48 formed in its anterior surface. Other structures may also be provided to aid in the flexibility of the tip 38.

As seen in FIG. 5, the elbow 24 has a round hole 50 in each side between the posterior portion 47 of the elbow and an anterior portion of the elbow. This hole 50 is provided so that in the event the opening 36 is occluded, air might still be available to a patient. Alternate forms of these holes may include a square configuration 52 illustrated in FIG. 6 or a cavity 54 extending to the opening 36 as illustrated in FIG. 7. In other embodiments these holes or cavities may be eliminated.

Figure 10:
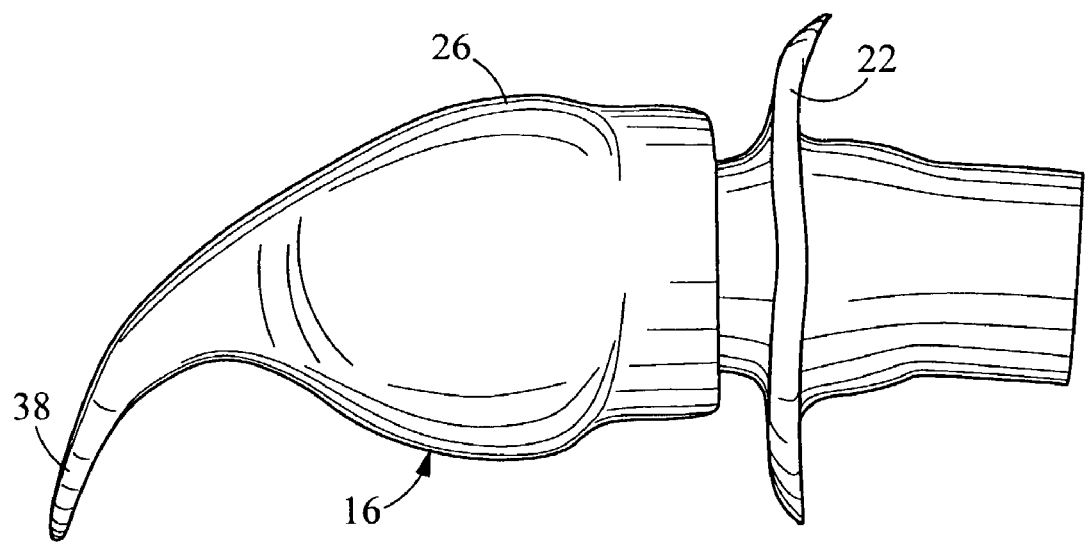
FIG. 10 is a side elevational view of the distal end of the perilaryngeal oral airway of FIG. 1 showing the tip and housing flexed in an anterior direction.

FIG. 10 illustrates the flexibility of the tip 38 and the housing 26. The tip 38 and the housing 16 are configured to deform and flex in the direction of the opening 16, or in an anterior direction.

Figure 11:
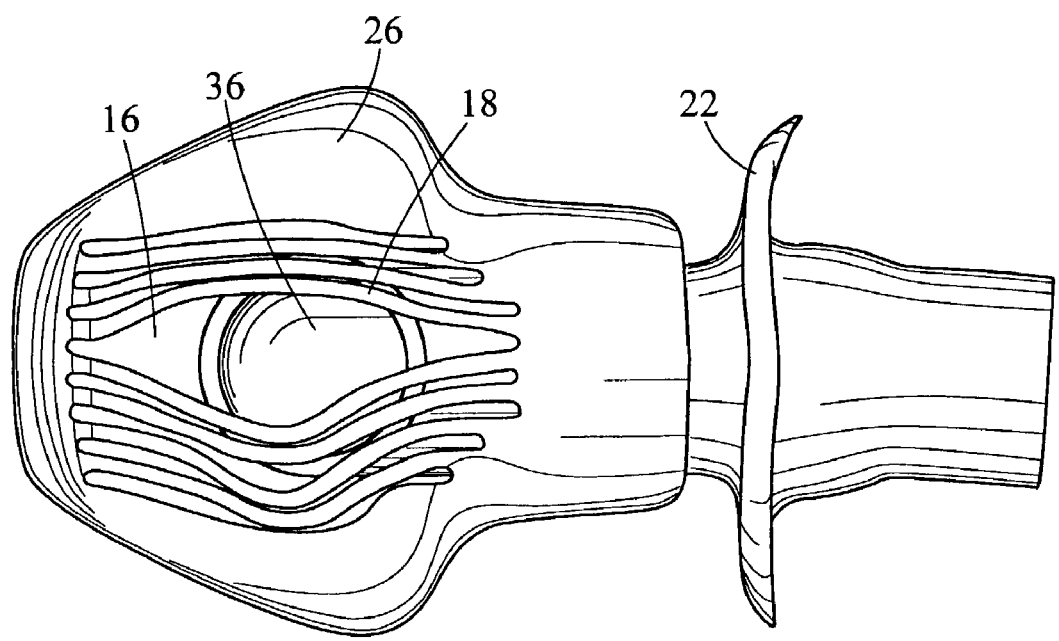
FIG. 11 is a bottom view of FIG. 10 illustrating lateral deflection of the flexible bars of the housing.

Flexibility of the housing in this direction is aided by the flexible bars 18 which, as illustrated in FIG. 11, deflect laterally as the housing 26 is flexed toward the opening 16. It should also be noted that as the housing is flexed the support ribs 44 separate at their distal ends to receive the posterior portion 47 of the elbow 24, which further aids the housing in bending about the elbow 24.

Figure 12:
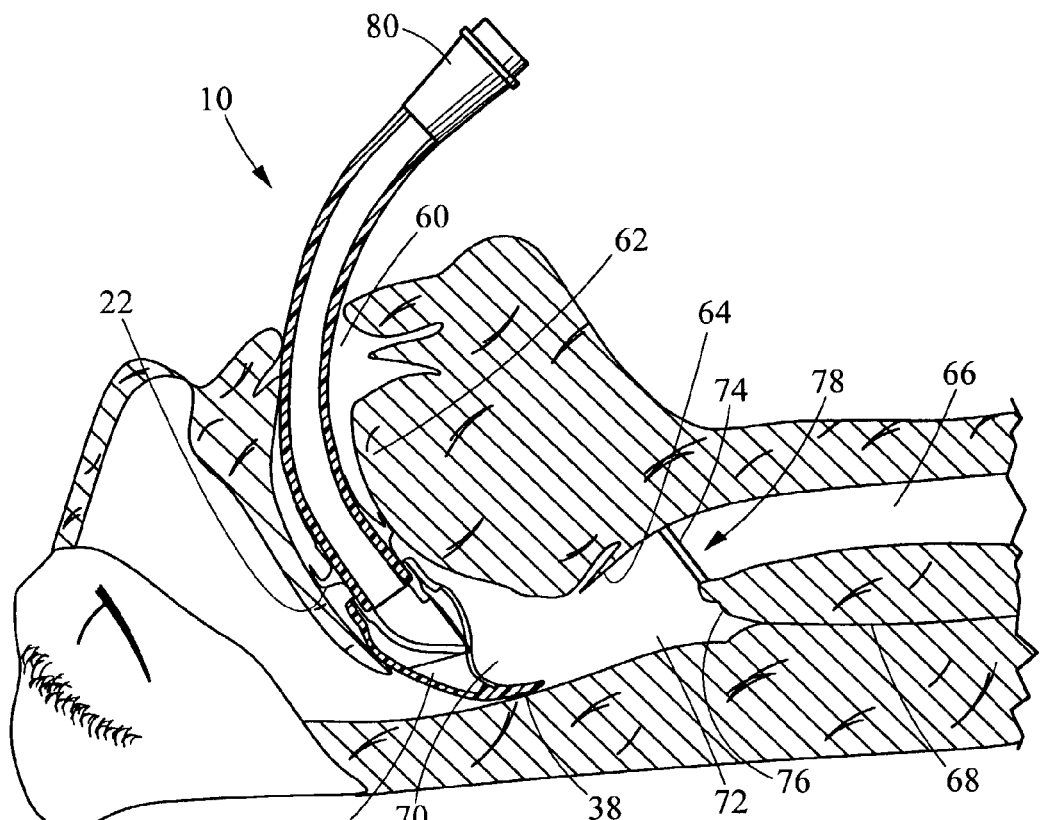
FIG. 12 is a cross-sectional side view illustrating insertion of the perilaryngeal oral airway of FIG. 1 into the mouth and throat of a patient.
Figure 13:
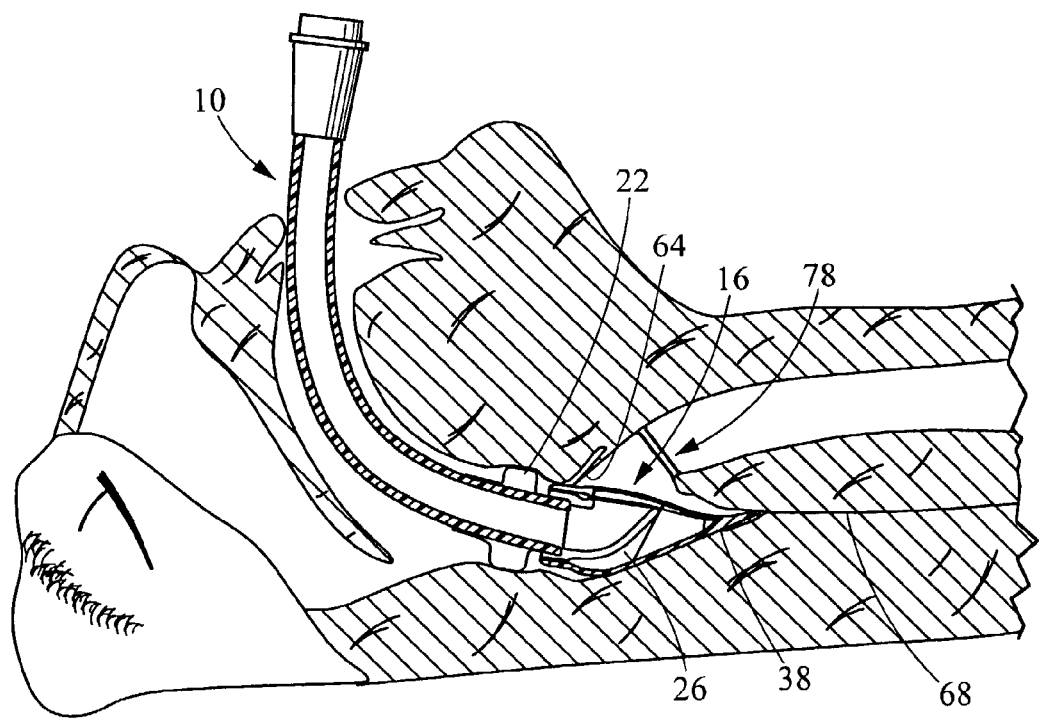
FIG. 13 is a cross-sectional side view illustrating the perilaryngeal oral airway of FIG. 1 seated within the hypopharynx of a patient.

FIGS. 12 and 13 illustrate insertion and seating of the PLA within a patient. FIG. 12 is a simplified anatomical illustration of a patient's head, including the oral airway defined by the oral cavity 60, the tongue 62, the epiglottis 64, the trachea 66, the esophagus 68, the pharynx 70, the hypopharynx 72, the vocal chords 74, the arytenoid cartilage 76 and the glottis or larynx indicated generally at 78. The various cartilage and muscular tissue comprising the glottis or larynx with the exception of the vocal chords 74, have been eliminated for the sake of clarity.

In use, the PLA is inserted with the housing leading into the mouth or oral cavity 60 of a patient. The flexible tip 38 guides the PLA over the tongue 62 and as the flexible tip 38 abuts the posterior wall of the pharynx 70, it flexes toward the opening 18 (or toward the larynx) as illustrated in FIG. 12. This abutment may further cause flexing of the housing 26 and lateral separation of the bars 18 as illustrated and described above with reference to FIGS. 10 and 11. The flexing of the tip 38 and the housing 26 effectively shortens the length of the housing, making it easier for the housing to make the bend into the hypopharynx. With further insertion of the PLA into the throat of the patient, the housing rebounds to its original shape and the flexible bars encounter the epiglottis 64 and the epiglottis rides up the flexible bars. Axial insertion of the housing is intended to be arrested by the sidewalls of the relatively enlarged proximal portion of the housing coming into abutment with the aryepiglottic folds within the hypopharynx 72. As illustrated in FIG. 13, with the PLA properly seated, the epiglottis abuts an anterior portion of the PLA, the flexible tip 38 is lodged in the opening of the esophagus 68 and the opening 16 of the housing 26 as well as the opening 36 of the elbow 24 are in close proximity to the vocal chords and the glottis or larynx 78. In this manner, all the soft tissue surrounding the hypopharynx and larynx is held back from the opening 16 and an unobstructed airway is provided to the trachea 66 for unassisted patient breathing.

The PLA can also be used to provide respiratory assist or anesthesia of a patient. In this application, once the PLA is seated as illustrated in FIG. 13, the inflatable cuff is inflated so as to form a seal in the patient's pharynx 72. In some instances, depending upon the patient's anatomy, the cuff may inflate within the hypopharynx. In FIG. 12 the cuff 22 is uninflated and the cuff is shown inflated in FIG. 13. Inflation of the cuff forms a seal allowing pressurized respiratory assist to a patient. A respiratory circuit or anesthesia circuit (not shown) as conditions require, may be attached to the distal end of the breathing tube by the adaptor 80.

Figure 14:
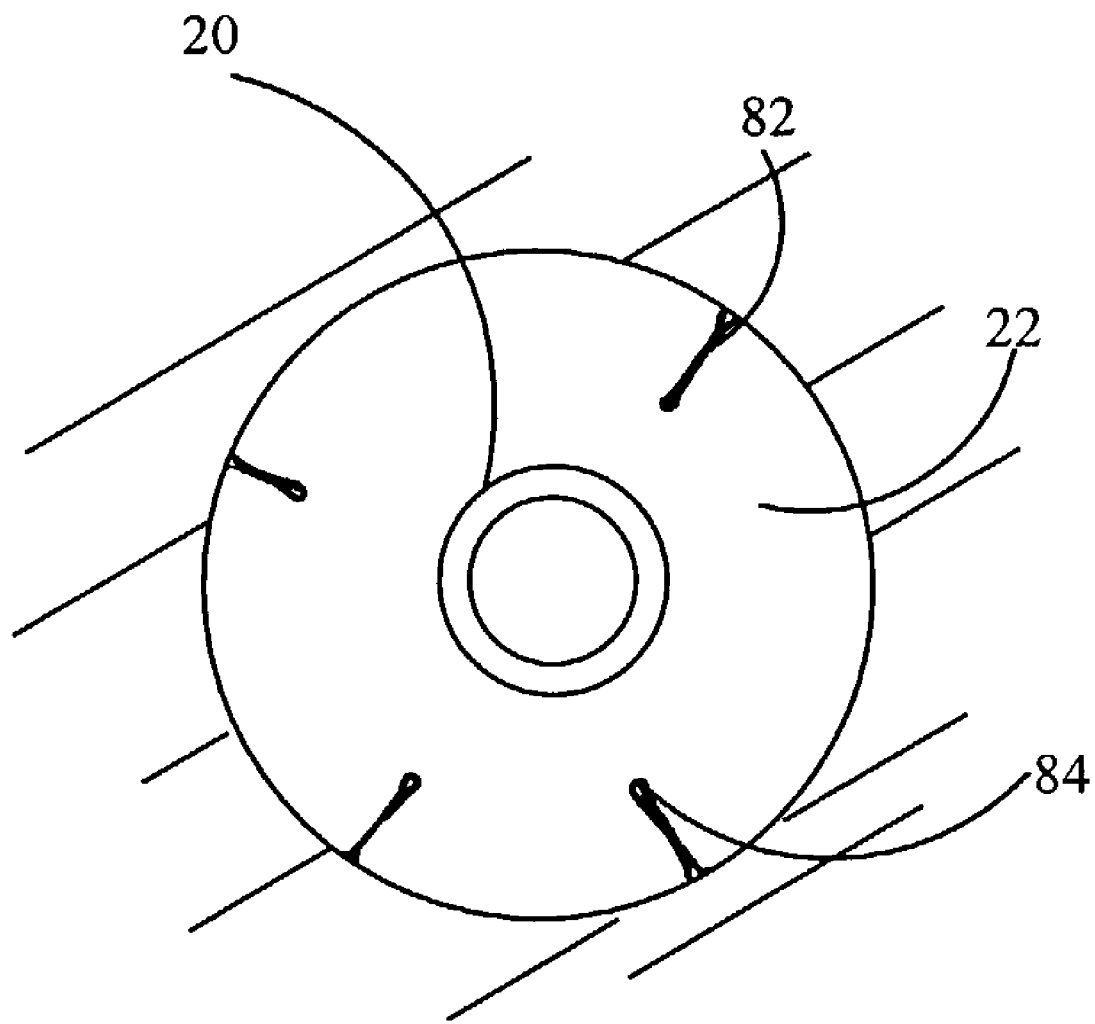
FIG. 14 is a cross-sectional view illustrating an inflated thin-walled cuff in the pharynx of a patient.

In one embodiment the cuff 22 may be made of a thin-walled foil having a thickness on the order of 0.03 to 0.005 mm or less. Suitable materials from which such a thin-walled cuff could be made include polyethylene terephthalate (PETP), low-density polyethylene (LDPE), polyvinyl chloride (PVC) or polyurethane (PU). Referring to FIG. 14, which is a cross-section of the inflated cuff 22, in a pharynx, the thin-walled foil 82 results in fold loops 84 having an extremely small diameter that effectively prevents the passage of liquids there-through and which minimizes the passage of air to effectively prevent breach of a seal formed in the pharynx or hypopharynx of a patient. The thin-walled foil is particularly useful because it enables use of a single over-sized diameter cuff that, when in an inflated state, can effectively be used to form a seal in different patients having different sized or shaped pharynx or hypopharynx.

The PLA 10 is also intended to allow blind intubation of a patient with an endotracheal tube or insertion of other instruments into the trachea of a patient. As can be appreciated by reference to FIG. 13, the breathing tube 20 and elbow 24 serve to direct an endotracheal tube or other instrument inserted axially within the PLA into the trachea 66 of a patient. The flexible bars 18 are flexible enough so that the endotracheal tube or instrument can be inserted into a gap between adjacent bars to deform the bars in a manner similar to that illustrated in FIG. 11. To aid in the passing of an instrument through the bars, the bars may be formed with lengthwise posterior facing apexes 86 as illustrated in FIG. 9. Or, as illustrated in FIG. 8, it may be sufficient for the flexible bars 18 to have a flat posterior surface 88.

What is claimed is:

1. An oral airway comprising:
   an elongate tubular member having a leading distal end and a proximal end, the leading distal end leading the elongate tubular member as it is inserted into the mouth and pharynx of a patient, there being an opening at the leading distal end that is inclined so that a posterior portion of the distal end extends beyond an anterior portion of the distal end; and
   a flexible tip portion extending distally beyond the opening from the posterior portion to aid insertion of the oral airway into the mouth and pharynx of a patient, the tip portion being tapered laterally from its proximal end to its distal end and further being configured to flex toward the opening as it abuts tissue within the mouth and pharynx of a patient, the flexible tip further comprising lateral grooves to contribute to its flexibility.

2. An oral airway comprising:
   an elongate tubular member having a leading distal end and a proximal end, the leading distal end leading the elongate tubular member as it is inserted into the mouth and pharynx of a patient, there being an opening at the leading distal end that is inclined so that a posterior portion of the distal end extends beyond an anterior portion of the distal end;
   a housing at the distal end of the elongate tubular member surrounding the opening; and
   a flexible tip portion attached to the housing extending distally beyond the opening from a posterior portion of the housing to aid insertion of the oral airway into the mouth and pharynx of an patient, the tip portion being tapered laterally from its proximal end to its distal end and further being configured to flex toward the opening as it abuts tissue within the mouth and pharynx of a patient.

3. The oral airway of claim 2 wherein the housing is configured to flex toward the opening about the distal end of the elongate tubular member as the tip abuts tissue as it is inserted into the mouth and pharynx of a patient.

4. The oral airway of claim 3 wherein the housing further comprises a pair of spaced ribs extending between an inner surface of a posterior wall and the posterior portion of the distal end of the elongate tubular member, the spaced ribs deflecting to receive the posterior portion of the distal end of the elongate tubular member as the housing is flexed toward the opening.

5. The oral airway of claim 3 wherein the housing defines a housing opening corresponding to the tubular member opening, the housing having a plurality of flexible bars covering the housing opening, the flexible bars deflecting as the housing member is flexed toward the opening.

6. The oral airway of claim 2 further comprising an elbow attached to the distal end of the elongate tubular member, the elbow defining the opening.

7. An oral airway comprising:
   an elongate tabular member having a leading distal end and a proximal end, the leading distal end leading the elongate tubular member as it is inserted into the mouth and pharynx of a patient;
   a housing at the distal end of the elongate tubular member, the housing having an anterior opening in communication with a lumen of the elongate tubular member and lateral side walls configured to abut the aryepiglottic folds within a patient's hypopharynx when fully inserted in the pharynx of a patient to seat the housing with the anterior opening adjacent to the patient's larynx; and
   a flexible tip portion extending distally from the housing beyond the opening to aid insertion of the oral airway into the mouth and pharynx of a patient, the tip tapering inward relative to the lateral side walls from its proximal to its distal end and the tip being configured to flex toward the opening as the flexible tip abuts tissue within the mouth and pharynx of a patient as it is inserted into the mouth and pharynx of the patient.

8. The oral airway of claim 7 wherein the flexible tip is integrally formed with the housing.

9. The oral airway of claim 8 wherein the flexible tip and housing are made of an elastomer having a durometer of about 80 Shore A or less.

10. The oral airway of claim 7 wherein the housing is configured to flex in an anterior direction as the flexible tip abuts tissue as it is inserted into the mouth and pharynx of a patient.

11. The oral airway of claim 10 further comprising a plurality of flexible bars covering the anterior opening, the flexible bars deflecting as the housing is flexed in an anterior direction.

* * * * *